(12) United States Patent
Moo-Young et al.

(10) Patent No.: US 7,393,689 B2
(45) Date of Patent: Jul. 1, 2008

(54) METHOD AND APPARATUS FOR CHARACTERIZING COAL TAR IN SOIL

(75) Inventors: Horace Keith Moo-Young, Breinigsville, PA (US); Derick Gerdts Brown, Bethlehem, PA (US); Andrew J. Coleman, San Francisco, CA (US)

(73) Assignee: Lehigh University, Bethlehem, PA (US)

( * ) Notice: Subject to any disclaimer, the term of this patent is extended or adjusted under 35 U.S.C. 154(b) by 921 days.

(21) Appl. No.: 10/766,497

(22) Filed: Jan. 27, 2004

(65) Prior Publication Data

US 2005/0164396 A1    Jul. 28, 2005

(51) Int. Cl.
    *G01N 33/24*    (2006.01)
(52) U.S. Cl. .................. 436/31; 73/152.18; 436/27; 436/28; 436/29; 436/139; 436/140
(58) Field of Classification Search .............. 73/152.11, 73/152.18, 152.41–152.42; 436/27–29, 31, 436/139–140, 5
    See application file for complete search history.

(56) References Cited

U.S. PATENT DOCUMENTS

| | | | | |
|---|---|---|---|---|
| 3,018,660 | A | * | 1/1962 | Schmid .................. 73/152.09 |
| 4,233,840 | A | * | 11/1980 | Goss et al. .............. 73/152.11 |
| 4,487,056 | A | * | 12/1984 | Wiley ............................ 73/38 |
| 4,672,840 | A | * | 6/1987 | Cullick .......................... 73/38 |
| 5,174,966 | A | * | 12/1992 | Durand et al. .............. 422/102 |
| 5,299,453 | A | * | 4/1994 | Sprunt et al. ............. 73/152.23 |
| 5,319,966 | A |  | 6/1994 | Jackson et al. |
| 5,363,692 | A | * | 11/1994 | Lafargue et al. ............... 73/38 |
| 5,587,324 | A |  | 12/1996 | Roy et al. |
| 5,687,093 | A |  | 11/1997 | Long et al. |
| 5,858,791 | A | * | 1/1999 | Lemaire ...................... 436/25 |
| 5,905,036 | A | * | 5/1999 | Pope et al. ................. 435/262 |
| 5,976,883 | A | * | 11/1999 | Schabron ..................... 436/28 |
| 6,321,595 | B1 |  | 11/2001 | Pope et al. |

OTHER PUBLICATIONS

Wright, B. W. et al, Energy & Fuels 1989, 3, 474-480.*
Cushey, M. A. et al, AIChE 1990 Summer National Meeting (San Diego Aug. 19-22, 1990) Preprint N.56e 26P.*
Lane, W. F. et al, Environmental Science and Technology 1992, 26, 983-990.*
Roy, S. B. et al, Water Environment Research 1995, 67, 4-15.*

(Continued)

*Primary Examiner*—Arlen Soderquist
(74) *Attorney, Agent, or Firm*—Kilpatrick Stockton LLP (57) ABSTRACT

The present invention provides a method and apparatus or system for determining an amount of coal tar that can enter, and subsequently be displaced from, a given type of soil for a range of depths of the soil. The method and apparatus also provide verification of the pressure at which coal tar can be displaced from a given type of soil. In particular, the method and apparatus simulate the hydrostatic pressure that a soil sample encounters in the subsurface of the ground. Accordingly, the method and apparatus provide a relationship between the concentration of coal tar in the soil and the pressure required to displace the coal tar from the soil, which allows for an estimation of the amount of coal tar that may be displaced at a particular location or site. Further, the method and apparatus are adaptable for use in the laboratory or the field.

16 Claims, 6 Drawing Sheets

OTHER PUBLICATIONS

Chiou, C. T. et al, Environmental Science and Technology 1998, 32, 264-269.*

Patrick, G. C. et al, Nonaqueous-Phase Liquids: Remediation of Chlorinated and Recalcitrant Compounds, International Conference on Remediation of Chlorinated and Recalcitrant Compounds, 1st, Monterey, Calif., May 18-21, 1998, 149-154, Editors: Wickramanayake, G. B. et al, Publisher: Battelle Press, Columbus, Ohio.*

Xia, G. et al, Environmental Science and Technology 1999, 33, 262-269.*

Walter, T. et al, Chemosphere 2000, 41, 387-397.*

Krauss, M, et al, Soil Science Society of America Journal 2002, 66, 430-437.*

Hawthorne, S. B. et al, Environmental Science and Technology 2003, 37, 3587-3594.*

Wisconsin Department of Health and Family Services, "Coal Tar Contamination Associate with a Former Manufactured Gas Plant Ashland/Northern States Power Lakefront", Public Comment Release, Dec. 6, 2001, 23 pgs.

National Risk Management Research Laboratory, "Western Research Institute Contained Recovery of Oily Wastes (CROW) Process (Innovative Technology Evaluation Report", Mar. 2000, 98 pgs.

"Assessing Sediment quality at Manufactured Gas Plant Sites", Wisconsin Department of Natural Resources, Mar. 1996, 20 pgs., Wisconsin DNR, Bureau of Watershed Management.

* cited by examiner

METHOD AND APPARATUS FOR CHARACTERIZING COAL TAR IN SOIL

BACKGROUND OF THE INVENTION

1. Field of the Invention

This invention relates to a method and apparatus for determining an amount of coal tar that can be displaced from a given type of soil for a range of depths of the soil. More particularly, the method and apparatus of the present invention relate to development of a relationship between the concentration of coal tar in the soil and the pressure required to displace the coal tar from the soil.

2. Description of the Related Art

Manufactured gas plants (MGPs) were typically built adjacent to streams, rivers and estuaries to supply towns with an energy source in the 1800's and continued operations until the 1960s when a network of gas pipelines was built across the country. Many MGPs were abandoned or demolished and left behind a large amount of waste and contamination that now pose a potential environmental problem. A byproduct of the gasification process was "coal tar," which is a mixture of polycyclic hydrocarbons (PAHs) and monocyclic hydrocarbons (MAHs).

The environmental concern over the presence of coal tar as a non-aqueous phase liquid (NAPL) in the subsurface of MGP sites is a subject of interest to both regulators and the companies they regulate. The concern is centered over whether the NAPL is trapped or can be displaced from the soil into a water source. If the NAPL can be displaced from within the soil, it may flow vertically through an aquifer or laterally down sloping fine-grained stratigraphic units and either directly into a water source or indirectly into a water source by providing an additional pressure that can displace the otherwise trapped NAPL.

The types and quantities of waste discharged from MGP plants that introduced coal tar into the environment are highly varied. Coal tars are complex mixtures of over 10,000 organic compounds of varying molecular weight, functional groups and characteristics, and less than 40% of these individual compounds can be quantified using common organic chemistry techniques because of the presence of pitch. See Lee, et al. *Env. Sci. and Tech.* 26:2110-2115 (1992). The pitch fraction of coal tar is significant in that many components within pitch are considered relatively insoluble but still enter water to the extent of their solubility.

State regulations have presented challenges to field personnel who must quickly, consistently and accurately identify, record and characterize coal tar within a test site. The most important concern is whether a coal tar is trapped or can be displaced from a given type of soil. There is little information in the literature regarding the point at which coal tar becomes trapped in a soil. Furthermore, there is no method or system that would provide one of skill in the art with a way of determining whether coal tar is trapped or can be displaced from a given type of soil from a variety of locations within a site. Accordingly, those of skill in the art would benefit from a method or system for the determination of the amount of coal tar that can enter, and subsequently be displaced from, a given type of soil for a range of depths of the soil, and verification of the pressure at which coal tar can be displaced from the given type of soil.

SUMMARY OF THE INVENTION

The present invention provides a method and apparatus or system for determining an amount of coal tar that can enter, and subsequently be displaced from, a given type of soil for a range of depths of the soil. The method and apparatus also provide verification of the pressure at which coal tar can be displaced from a given type of soil. In particular, the method and apparatus simulate the hydrostatic pressure that a soil sample encounters in the subsurface of the ground. Accordingly, the method and apparatus provide a relationship between the concentration of coal tar in the soil and the pressure required to displace the coal tar from the soil, which allows for an estimation of the amount of coal tar that may be displaced at a particular location or site. Further, the method and apparatus are adaptable for use in the laboratory or the field.

In one embodiment, the present invention provides a method for determining an amount of coal tar that can enter a given type of soil at a range of soil depths at a field site, comprising: placing a soil sample free of coal tar from a site in a pressurizable chamber; filling the pressurizable chamber with water, thereby displacing gas from the pressurizable chamber; feeding coal tar at a first predetermined pressure to the pressurizable chamber, thereby pressurizing the soil sample to the first predetermined pressure and displacing a portion of the water with the coal tar to create an amount of displaced water; measuring the amount of the displaced water to determine an amount of coal tar that entered the soil sample; repeating said feeding and said measuring at a plurality of additional predetermined pressures to provide a plurality of pressures and corresponding amounts of coal tar that entered the soil sample; and correlating each of said pressures to a depth of soil at a field site to determine an amount of coal tar that can enter the soil at a range of soil depths at the field site.

In another embodiment, the present invention provides a method for determining an amount of coal tar that can be displaced from a soil sample at a range of soil depths at a field site, comprising: placing a soil sample comprising a known amount of coal tar in a pressurizable chamber; removing gas from the soil sample; feeding water at a first predetermined water pressure to the pressurizable chamber, thereby pressurizing the soil sample to the first predetermined water pressure and displacing a portion of the coal tar from the sample to product an amount of displaced coal tar; measuring the amount of displaced coal tar; repeating said feeding water and said measuring the amount of displace coal tar at a plurality of additional predetermined water pressures, thereby generating a plurality of water pressures and corresponding amounts of displaced coal tar; and correlating each of said water pressures to a depth of soil at the field site to determine an amount of coal tar that can be displaced from the soil sample at a range of soil depths at the field site.

In another embodiment, the present invention provides an apparatus, adaptable for positioning in the laboratory or the field, for determining an amount of coal tar that can enter, and subsequently be displaced from, a given type of soil for a range of depths of the soil, comprising: a pressurizable chamber configured to hold a soil sample; at least two reservoirs fluidly connected to said pressurizable chamber and configured to feed a pressurized fluid to said pressurizable chamber; and a source of controlled pressure fluidly connected to each of said at least two reservoirs.

DETAILED DESCRIPTION OF THE PREFERRED EMBODIMENTS

As discussed in more detail below, the invention generally comprises a method and apparatus or system for determining an amount of coal tar that can enter, and subsequently be displaced from, a given type of soil for a range of depths of the soil. The method and apparatus also provide verification of the pressure at which coal tar can be displaced from a given type of soil. In particular, the method and apparatus simulate the hydrostatic pressure that a soil sample encounters in the subsurface of the ground. Accordingly, the method and apparatus provide a relationship between the concentration of coal tar in the soil and the pressure required to displace the coal tar from the soil, which allows for an estimation of the amount of coal tar that may be displaced at a particular location or site. Further, the method and apparatus are adaptable for use in the laboratory or the field.

The following text in connection with the Figures describes various embodiments of the present invention. The following description, however, is not intended to limit the scope of the present invention. It should be appreciated that where the same numbers are used in different figures, these refer to the same element or structure. It should be appreciated that in the following description, the concentration of coal tar in a sample of soil is the amount of coal tar in the total void space within the sample and is expressed herein as percent coal tar. The amount of coal tar entering, and subsequently displaced from, a given sample of soil is expressed herein as a change in the percentage of coal tar in the sample.

Figure 1:
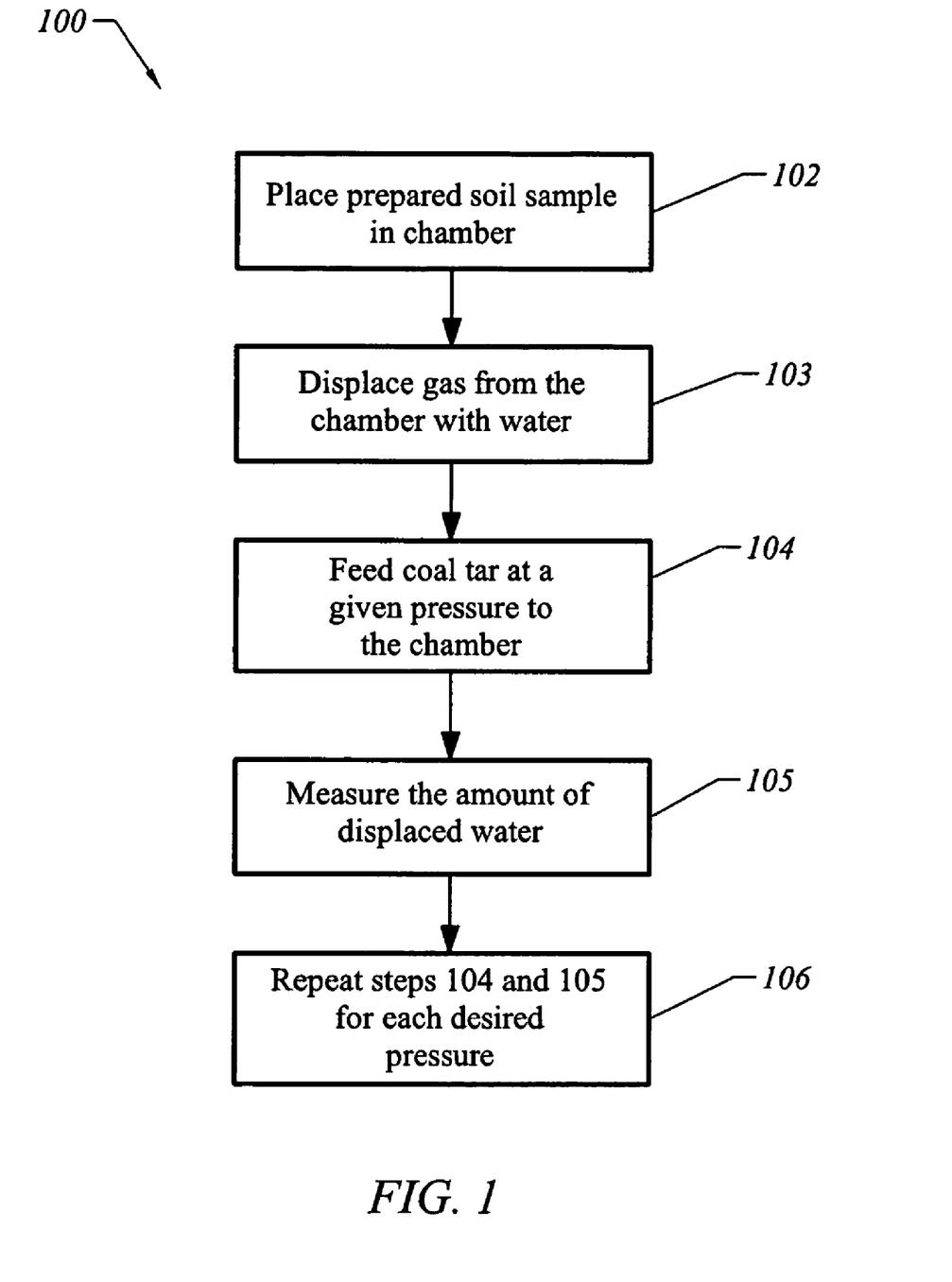
FIG. 1 is a flowchart illustrating a method of determining an amount of coal tar that can enter a given type of soil, according to one embodiment of the present invention.

FIG. 1 is a flowchart illustrating a method of determining an amount of coal tar that can enter a given type of soil, according to one embodiment of the present invention. More particularly, this method allows for the determination of the amount of coal tar that can enter a given type of soil by feeding coal tar into a soil sample at incrementally higher pressures. Generally, a graphical representation or curve may be generated illustrating the relationship between the amount of coal tar that can be forced into a given soil sample and the pressure required to force that amount of coal tar into the sample. This curve is generated by obtaining the quantity of water that is pushed out of the sample under a given stress or pressure from the entering coal tar. These pressures can be related to soil depth at a field location or site to allow the determination of the depth at which coal tar may be present in the soil. For example, a given pressure may be required to force a certain amount of coal tar into a particular soil sample to produce a given coal tar concentration in the soil. This pressure may be related to pressure experienced by the soil at a particular depth below the soil surface at a particular field location. It may then be concluded that soil at or below this depth would be capable of having that same coal tar concentration or more. In addition, knowing the coal tar concentration of a soil sample and the depth at which it was taken, this method can be used to determine whether the soil at that depth could hold additional coal tar. For example, if the soil sample obtained at a given depth contained a concentration of coal tar that was less than the concentration of coal tar measured at a corresponding pressure using the method of the present invention, then the soil at that depth may be capable of holding additional coal tar. It should be appreciated, however, that disruptions to the soil, either natural or man-made would affect this type of analysis.

The first step 102 of the method 100 of FIG. 1 comprises placing a prepared soil sample from a field site in a pressurizable chamber. It should be appreciated that this soil sample should be free of coal tar, which can be verified by analytical techniques. The soil sample may be obtained from the site at depths of up to about 300 feet below the surface. In a preferred embodiment, the sample is obtained at depths of up to about 100 feet below the surface. The first sample is oven-dried at a temperature of about 105° C. to about 110° C. for at least 12 hours, and the amount of the first sample placed into the pressurizable chamber is recorded.

It should be appreciated that the first sample may be obtained using any device known to one of skill in the art for obtaining soil samples. Core sampling devices that might be used to collect soil samples include, but are not limited to, gravity corers, vibracorers, piston corers or a hollow-stem auger drill with a split-spoon sampler. The method of obtaining soil samples should be consistent to the extent that each of the soil samples in a sample set are obtained such that they have comparable densities, since a variation in the density of the soil sample can create a variation in the results of the present invention. Furthermore, the temperature at which the sample may be oven dried and the duration of drying may vary depending upon the given type of soil. The preferred temperature to oven dry the soil is from about 60° C. to about 110° C. to avoid thermal degradation of components within the soil.

After placing the first sample in the pressurizable chamber, the next step 103 comprises filling the pressurizable chamber with water, thereby displacing gas from the pressurizable chamber. The gas is displaced by allowing the first sample to equilibrate with a positive pressure of water entering one end of the pressurizable chamber and a back-pressure of water entering an opposite end of the pressurizable chamber. Normally, it takes from approximately one hour to three days for the first sample and water to reach equilibrium. Equilibrium occurs, for example, when there are no air bubbles exiting the system in the effluent line of the chamber.

It should be appreciated that any method of displacing gas from the chamber may be used in the methods of the present invention. For example, the gas may be displaced using vacuum and replacing the displaced gas with water. In another example, the gas may also be displaced by repetitive freezing and thawing, which can be accomplished in a freeze-drying apparatus. In another example, the sample and water can be heated in the chamber to displace gas. Accordingly, the time to displace gas from the first sample can vary with variation with the method chosen.

After filling the pressurizable chamber with water, thereby displacing gas from the pressurizable chamber, the next step 104 comprises feeding coal tar at a first predetermined pressure to the pressurizable chamber using compressed air. The first sample is pressurized to the first predetermined pressure, thereby displacing the water with the coal tar to create an amount of displaced water.

It should be appreciated that any form of pressure, positive or negative, may be used to feed coal tar into the pressurizable chamber. For example, any gas can be used to provide a positive pressure including, but not limited to, compressed air and inert gases such as nitrogen, argon, helium or neon. In another example, the pressure can be applied mechanically with an apparatus such as a pump or press. In another example, the pressure can be negative pressure from a vacuum if the water vapor pulled from the first sample is trapped in a condenser for purposes of later measuring the amount of displaced water.

After feeding coal tar at the first predetermined pressure, thereby displacing the water with the coal tar to create an amount of displaced water, the next step 105 is measuring the amount of displaced water by observing a change in water level in an attached reservoir or effluent chamber. The amount of water displaced from the soil sample is equal to the volume amount of coal tar entering the soil sample. Knowing the oven-dried weight of the soil sample allows for calculation of the concentration of coal tar in the soil sample at the first predetermined pressure.

It should be appreciated that the amount of displaced water can be measured in any manner known to one of skill in the art. For example, the amount of displaced water can be measured volumetrically or gravimetrically. Further, it should be appreciated that the sample must reach equilibrium after applying a predetermined pressure before the amount of displaced water is measured. Equilibrium can take, for example, from about one minute to one week. To determine when equilibrium has been reached, the effluent chamber is monitored for the presence of air bubbles. In addition, if the volume in the effluent chamber remains constant at the particular pressure, equilibrium has been reached. It should be appreciated, however, that when performing this procedure in the field, leachate is collected at each given pressure noting that the system may not have reached equilibrium. Therefore, the field test is viewed as a dynamic test and provides relative information about the pressure required to force coal tar into a given soil sample.

The next step is repeating 106 the steps of feeding coal tar 104 and measuring displaced water 105 at a plurality of additional pressures to provide a range of pressures corresponding to a range of depths of the soil at the field site. The maximum pressure is reached when the amount of displaced water reaches an asymptotic minimum, indicating that the total amount of coal tar entering the sample has reached an asymptotic maximum.

The range of pressures applied may include from about 0.01 psi to about 100 psi or any range therein. In a preferred embodiment, the range of pressures is from about 0.01 psi to about 60 psi, or any range therein. As indicated above, it should be appreciated that the pressures applied to the samples can be a positive pressure or a negative pressure. Accordingly, if a negative pressure is used, the maximum pressure will be limited to atmospheric pressure.

Figure 2:
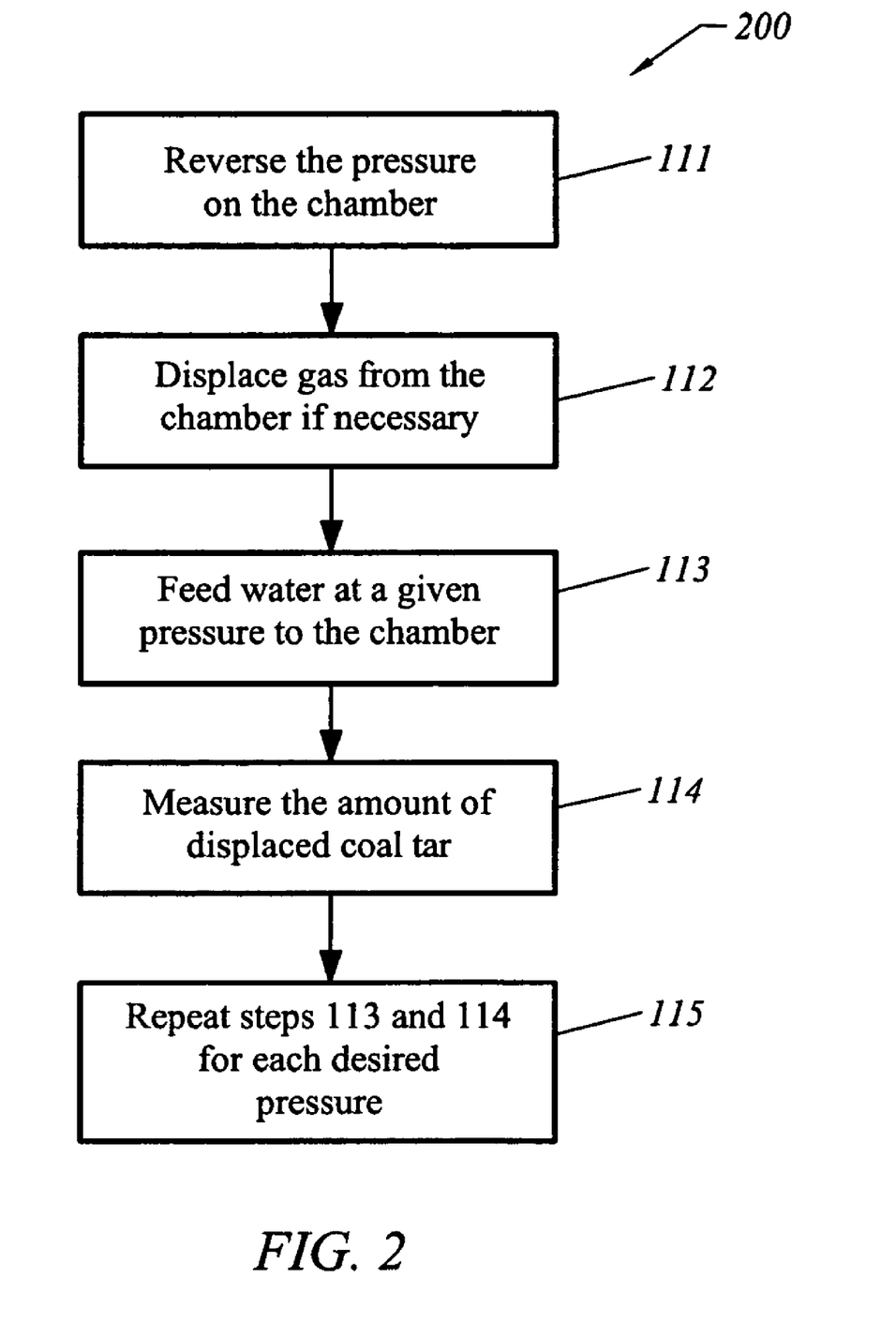
FIG. 2 is a flowchart illustrating a method of determining an amount of coal tar that can be displaced from a given type of soil, according to another embodiment of the present invention.

FIG. 2 is a flowchart illustrating a method of determining an amount of coal tar that can be displaced from a given type of soil, according to another embodiment of the present invention. More particularly, this method allows for the determination of the amount of coal tar that can be displaced from a given type of soil by displacing coal tar from a soil sample containing a maximum amount of coal tar. In essence, this method is the reverse of the method described in connection with FIG. 1, and the soil sample containing a maximum amount of coal tar may be generated by the method described in connection with FIG. 1. Generally, a graphical representation or curve may be generated illustrating the relationship between the amount of coal tar that may be displaced from a given soil sample and the pressure required to displace that amount of coal tar. This curve is generated by measuring the quantity of coal tar that is pushed out of the sample under a given stress or pressure. The coal tar in the soil sample is displaced by feeding water into the sample at incrementally higher pressures. These pressures can also be related to soil depth at a field location or site to allow the determination of the depth at which coal tar may be capable of mobility within the soil. Again, it should be appreciated, however, that disruptions to the soil, either natural or man-made would affect such an analysis.

As noted above, the method 200 begins with a soil sample that has a maximum amount of coal tar and may be prepared using the method of FIG. 1. Therefore, the first step 111 in the method 200 of FIG. 2 begins with the soil sample that is in the chamber at the end of the method 100 of FIG. 1. The first step 111, therefore, is reversing the direction of pressure on the soil sample in the pressurizable chamber to displace the coal tar from the sample.

It should be appreciated that a relationship between the concentration of coal tar in the soil and the pressure required to displace the coal tar from the soil can begin at any coal tar concentration. Accordingly, it is possible to start with a soil sample having a maximum concentration of coal tar that has been prepared by another method or simply to start with a soil sample that has any concentration of coal tar in it, such as a field sample containing coal tar. The amount of coal tar in the sample can be determined in the laboratory using procedures known to one of skill in the art including, but not limited to, solvent extraction and gravimetric procedures. A sample from a field site, however, will require displacing gas 112 from the sample in the manner discussed above before proceeding with determining an amount of coal tar that can be displaced from the first sample at a range of predetermined water pressures.

After reversing the direction of pressure on the first sample comprising a known amount of coal tar in the pressurizable chamber and displacing gas if necessary, the next step 113 is feeding the water at a first predetermined pressure to the pressurizable chamber. The sample is pressurized to the first predetermined pressure, thereby displacing the coal tar with the water to create an amount of displaced coal tar. As described above in connection with FIG. 1 and feeding coal tar under pressure, it should be appreciated that any form of pressure, positive or negative, may be used to feed water into the pressurizable chamber.

After feeding water at the first predetermined pressure, thereby displacing the coal tar with the water to create an amount of displaced coal tar, the next step 114 is measuring the amount of displaced coal tar by observing a change in coal tar level in an attached reservoir. The amount of coal tar displaced from the sample is equal to the amount of water entering the sample. Knowing an oven-dried amount for the sample without coal tar allows for calculation of the amount of coal tar that can be displaced from the sample at the first predetermined pressure. As described above in connection with FIG. 1 and the measurement of displaced water, it should be appreciated that the amount of displaced coal tar can also be measured in a similar manner.

The next step 115 is repeating the feeding of water 113 and the measuring of displaced coal tar 114 at a plurality of additional water pressures to provide a range of water pressures corresponding to a range of depths of the soil. The maximum pressure is reached when the amount of displaced coal tar reaches an asymptotic minimum, indicating that the total amount of coal tar displaced from the sample has reached an asymptotic maximum.

The range of pressures applied may include from about 0.01 psi to about 100 psi or any range therein. In a preferred embodiment, the range of pressures is from about 0.01 psi to about 60 psi, or any range therein. As indicated above, it should be appreciated that the pressures applied to the samples can be a positive pressure or a negative pressure. Accordingly, if a negative pressure is used, the maximum pressure will be limited to atmospheric pressure.

Figure 3:
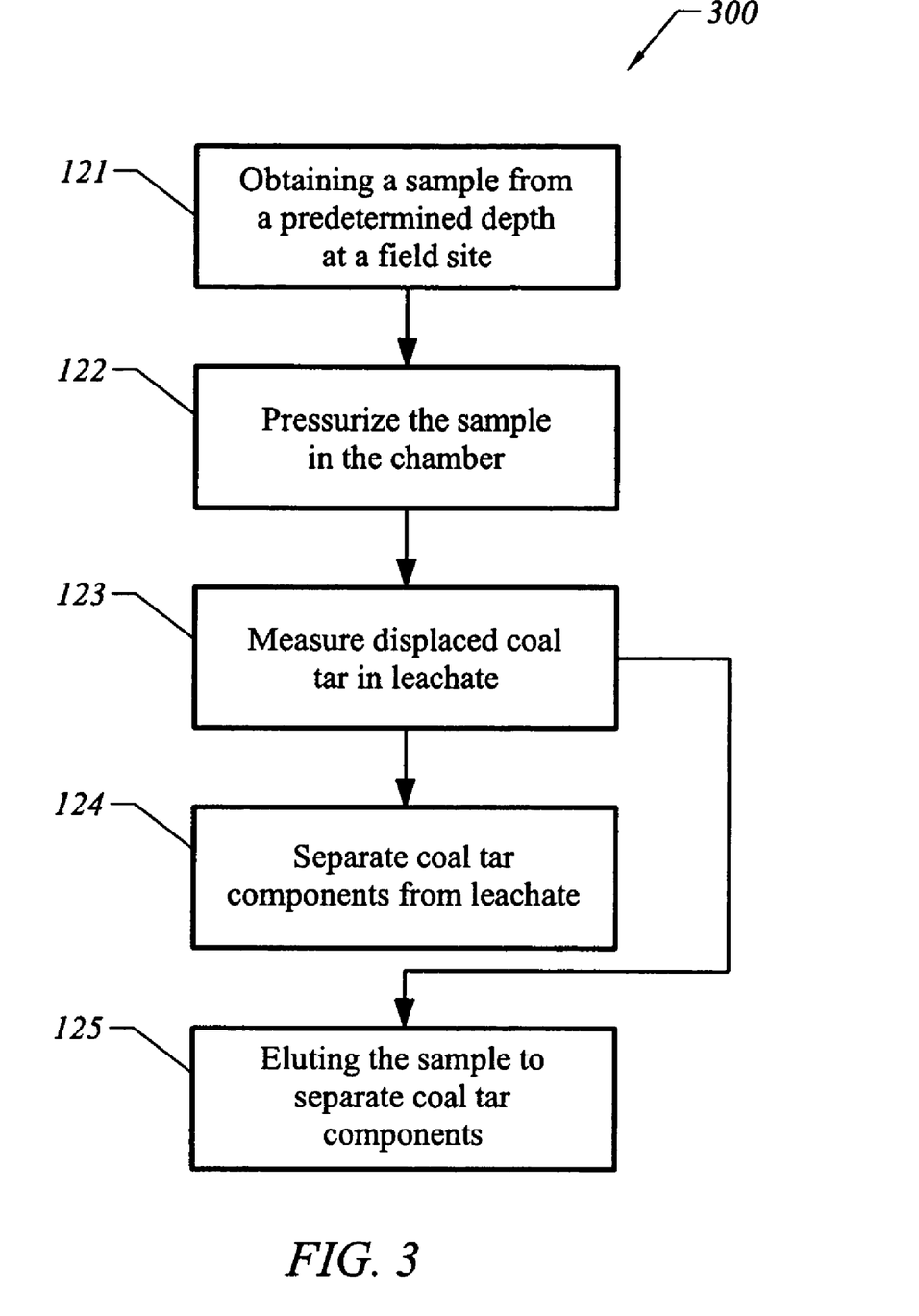
FIG. 3 is a flowchart illustrating a method of verifying that an amount of coal tar displaced from a sample from the site at a given depth is approximately the same as the amount of coal tar displaced in accordance with the method of FIG. 1.

FIG. 3 is a flowchart illustrating a method of verifying that an amount of coal tar displaced from a sample from the site at a given depth is approximately the same as the amount of coal tar displaced in accordance with the method of FIG. 1. It should be appreciated that this method can be performed using the same apparatus as the methods described in connection with FIGS. 1 and 2.

The method 300 comprises the first step 121 of obtaining an additional sample from a predetermined depth within a field site that contains coal tar. The next step 122 is pressurizing the sample comprising coal tar in the chamber at a pressure approximately equivalent to a pressure at the predetermined depth to displace leachate. The next step 123 is measuring the amount of the displaced coal tar in the leachate, wherein the pressure at the predetermined depth is estimated using calculations known to one of skill in the art.

An optional step 124 of separating the components of the leachate that can pass through a hydrophilic filter provides for separation of coal tar components that are the most soluble in a solvent such as water in order to, for example, identify the most likely sources of contamination of a water supply. In a preferred embodiment, the hydrophilic filter is a paper filter. It should be appreciated that other hydrophilic filters can be used including, but not limited to, porous glass filters.

Another optional step 125 of eluting the sample with a solvent, preferably water, provides another way to extract components of the coal tar from the sample for analysis. It should be appreciated that the choice of solvent is dependent upon the components that are being extracted. In a preferred embodiment, water is used to extract and identify soluble leachate components that are most likely to contaminate groundwater. In another embodiment, dichloromethane, alcohol or methanol may be used, for example, to extract all of the coal tar from the sample for analysis.

The analysis of the coal tar components is provided using gas chromatography and flame ionization detection (GC/FID). It should be appreciated that any instrumentation known to one of skill in the art can be used to analyze the components of the coal tar including, but not limited to, gas chromatography, flame ionization detection, high pressure liquid chromatography, mass spectroscopy, UV spectroscopy, infrared spectroscopy, nuclear magnetic resonance, fluorescence, thermogravimetric analysis, calorimetery or combinations thereof.

Figure 4:
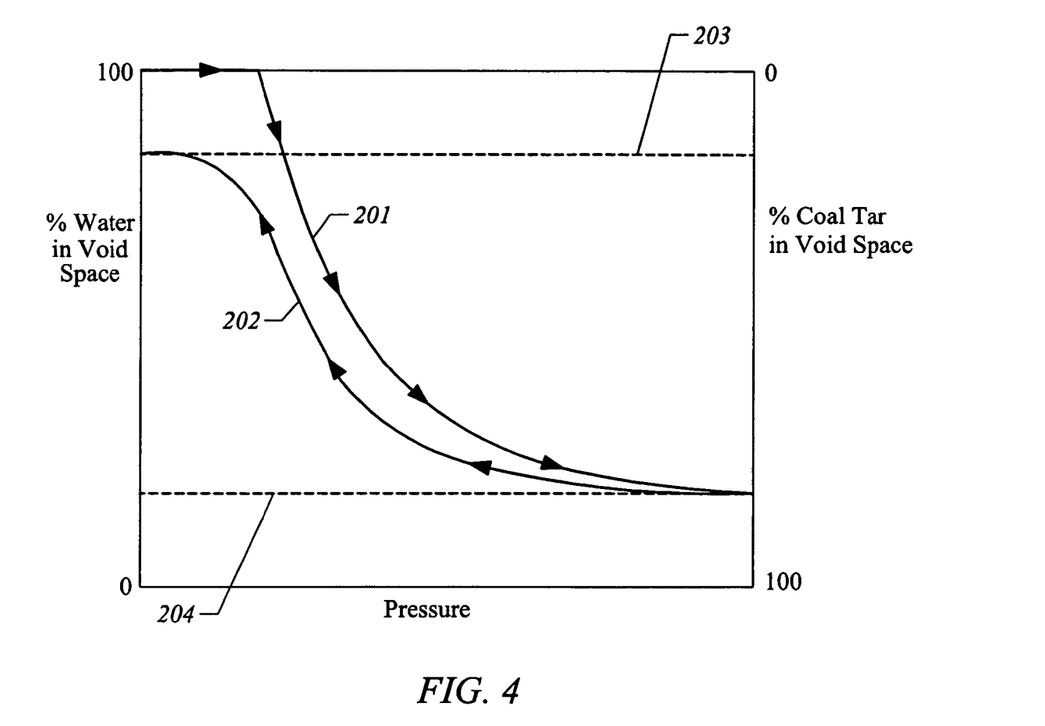
FIG. 4 illustrates a hysteresis relationship between an amount of coal tar that can enter, and subsequently be displaced from, a given type of soil at a plurality of predetermined pressures corresponding to a range of depths of the soil, according to one embodiment of the present invention.

FIG. 4 illustrates a hysteresis relationship between an amount of coal tar that can enter, and subsequently be displaced from, a given type of soil at a plurality of predetermined pressures corresponding to a range of depths of the soil, according to one embodiment of the present invention. The hysteresis relationship is produced using the method 100 described in connection with FIG. 1 and the method 200 described in connection with FIG. 2. It should be appreciated that the horizontal axis is pressure; however, for the downward curve 201, the pressure increases from the left to the right and for the upward curve 202, the pressure increases from right to left.

The method 100 described in connection with FIG. 1 is used to develop the downward curve 201, which represents an amount of coal tar that can enter a given type of soil for a range of depths of the soil. As indicated in FIG. 4, downward curve 201 begins with the sample saturated such that 100% of the void space within the sample is filled with water due to the displacing gas step 103 described above. Feeding the coal tar at a first predetermined pressure 104, measuring the amount of displaced water 105, and repeating these steps 104, 105 provides the data points that constitute the downward curve 201. Dashed line 204 indicates a maximum coal tar concentration where the amount of displaced water reaches an asymptotic minimum for the increase to the maximum pressure such that the total amount of coal tar entering the first sample has reached an asymptotic maximum.

The method 200 described in connection with FIG. 2 is used to develop the upward curve 202, which represents an amount of coal tar that can be displaced from a given type of soil for a range of depths of the soil. As indicated in FIG. 4, upward curve 202 begins with the sample containing the maximum coal tar concentration indicated by the dashed line 204. Feeding the water at a first predetermined water pressure 113, measuring the amount of displaced coal tar 114, and repeating these steps 113, 114, provides the data points that constitute upward curve 202. Dashed line 203 indicates a minimum coal tar concentration such that the total amount of coal tar displaced from the first sample has reached an asymptotic maximum.

The hysteresis relationship of FIG. 4 is useful in that it provides a way to determine (1) whether coal tar can be displaced from a given type of soil at a particular depth when the coal tar concentration is known at that depth; (2) the concentration of coal tar in a given type of soil when the pressure required to displace the coal tar from the given type of soil is known; (3) the maximum amount of coal tar that can enter a given type of soil; and (4) the maximum amount of coal tar that can be displaced from a given type of soil. For example, from these curves, the minimum pressure at which the coal tar is at equilibrium in the soil is known. Any pressure above this minimum pressure would force the coal tar to move in soil. In other words, soil found at a particular depth wherein the pressure on the soil is above this minimum pressure may be capable of forcing the coal tar in the soil to move. Alternatively, if the coal tar is bound to the soil or if the soil is at a depth wherein the pressure is below this minimum pressure, then the coal tar would not be expected to be mobile.

Accordingly, the hysteresis relationship illustrated in FIG. 4 provides one of skill in the art with a way of determining the amount of coal tar that can enter, and subsequently be displaced from, a given type of soil for a range of depths of the soil, and verifying the pressure at which coal tar can be displaced from the given type of soil. In particular, the hysteresis relationship illustrates a simulation of the pressure that a sample encounters in the subsurface and provides a relationship between the concentration of coal tar in the soil and the pressure required to displace the coal tar from the soil, and this relationship allows for, inter alia, as described above, a determination of whether coal tar can be displaced from the soil at a particular location on a site.

Figure 5:
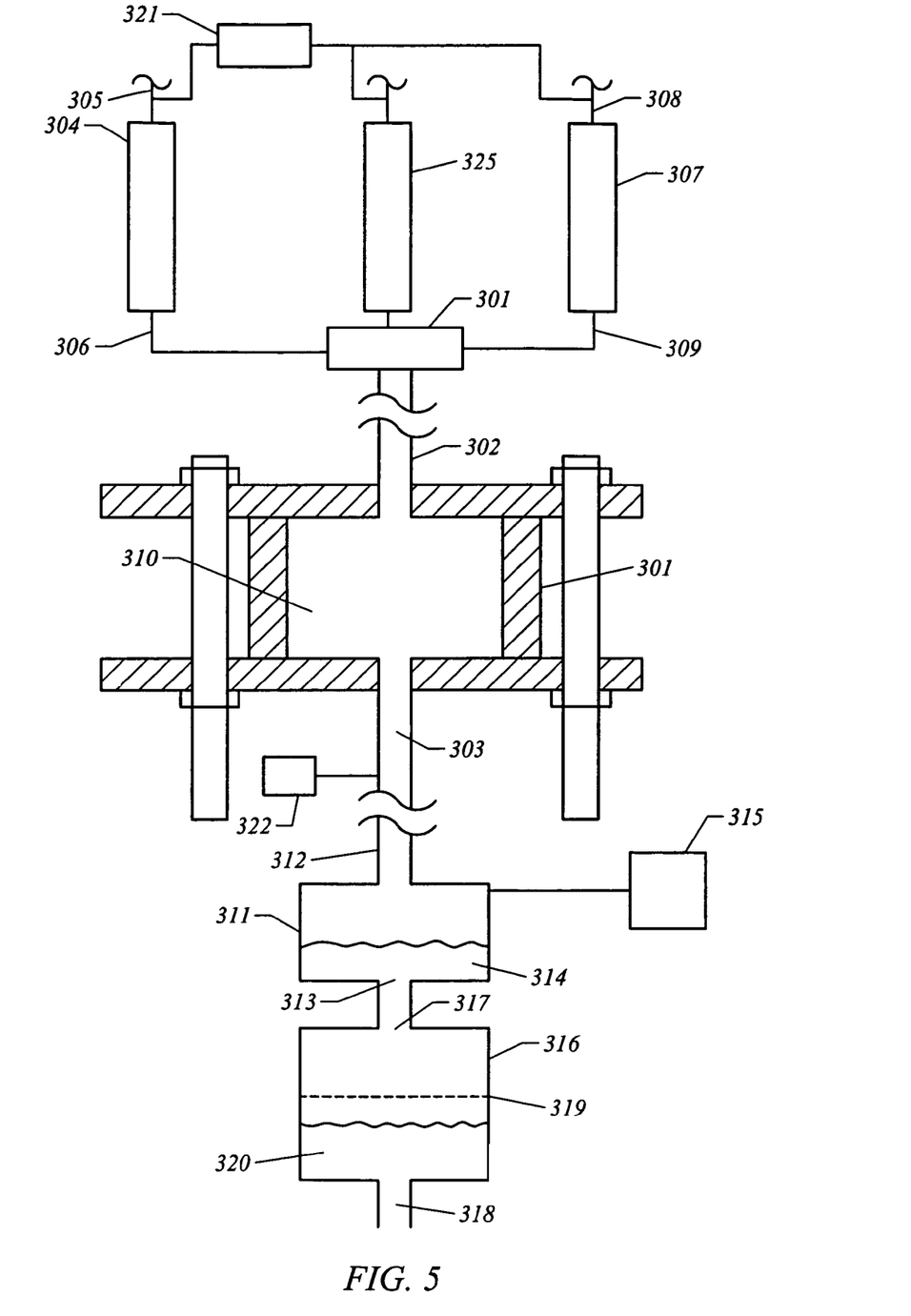
FIG. 5 illustrates a system for determining an amount of coal tar that can enter, and subsequently be displaced from, a given type of soil for a range of depths of the soil, and verifying the pressure at which coal tar can be displaced from the given type of soil, according to one embodiment of the present invention.

FIG. 5 illustrates a system for determining an amount of coal tar that can enter, and subsequently be displaced from, a given type of soil for a range of depths of the soil, and verifying the pressure at which coal tar can be displaced from the given type of soil, according to one embodiment of the present invention. The major components of the system are a chamber 301, a first reservoir 304 adaptable for connection to the chamber 301, a second reservoir 307 adaptable for connection to the chamber 301, a container 311 adaptable for connection to the chamber, a hydrophilic filter 316 adaptable for connection to the chamber 310 and the container 311, and a source of controlled pressure 321. It should be appreciated that the controlled source of pressure can be a source of positive pressure that is connected to the first reservoir inlet 305 or the second reservoir inlet 307. Alternatively, the source of controlled pressure 321 may be connected to the inlet 302 to the chamber 301 (not shown). Alternatively, the controlled source of pressure may be a controlled source of negative pressure connected downstream of the chamber 301, which is discussed in more detail below.

For purposes of developing the hysteresis relationship in the embodiment of FIG. 2, the system is comprised of the chamber 301 connected to the first reservoir 304 and the second reservoir 307 ("the reservoirs"). The reservoirs are adaptable for connection to the source of controlled pressure 321 and are connected to the chamber 301 by connecting first reservoir inlet 305 to chamber inlet 302 and by connecting second reservoir inlet 308 to chamber outlet 303, each of which are connected using a flexible and pressurizable tubing such as nylon braided Tygon® tubing.

Preferably, the chamber 301 is essentially a cylinder that is pressurizable up to at least 500 psi. The chamber 301 has an inner diameter of approximately 3 inches, an outer diameter of approximately 4 inches, and a height of approximately 2 inches. The soil samples that are placed in the chamber 301 are separated from the leachate and prevented from passing through either the chamber inlet 302 or the chamber outlet 303 by the implementation of two 200 sieve stainless steel screens. The interior of the chamber 301 is comprised of Teflon®. The function of the chamber is to contain a sample while pressurizing the sample to the predetermined coal tar pressures or predetermined water pressures as described above in method 100 discussed in connection with FIG. 1 and method 200 discussed in connection with FIG. 2.

It should be appreciated that chamber 301 can be a pressurizable container of any size, configuration and material that will provide the intended function of the present invention. In one example, the entire structure of the chamber 301 is stainless steel. In another example, the chamber 301 comprises acrylic components in combination with stainless steel structural support. In another example, the chamber 301 is capable of withstanding less than 500 psi.

The first reservoir 304 and second reservoir 307 are each a burette, and each is pressurizable up to at least 200 psi. Each burette has an inner diameter of approximately 0.5 inches, a height of approximately 24 inches, and is translucent to allow for visually measuring the amount of water or coal tar displaced from a sample. The function of the reservoirs is feeding water at predetermined water pressures, feeding coal tar at predetermined coal tar pressures, and collecting the displaced water and coal tar from a sample under pressure in order to measure the amount of water and coal tar displaced as described above in method 100 discussed in connection with FIG. 1 and method 200 discussed in connection with FIG. 2. To accomplish this, a manifold 301 is used to direct fluid flow from the reservoirs to the chamber inlet 302 and from the chamber outlet 303 back to the reservoirs. (The connection from the chamber outlet 303 to the manifold 301 is not shown.) It should be appreciated that a third reservoir 325 may alternatively be used to receive fluid from the chamber outlet 303 for measurement.

It should be appreciated that the reservoirs can be of any size, configuration and material that will provide the intended function of the invention. In one example, the reservoirs are not translucent and merely collect the water or coal tar for a gravimetric determination of the amount of water or coal tar displaced. In another example, the reservoirs are a combination of a translucent inner sleeve and a stainless steel outer sleeve to enable the reservoirs to withstand high pressures.

For purposes of verifying the pressure at which coal tar can be displaced from the given type of soil, the system is comprised of the chamber 301 connected to container 311, wherein both the chamber 301 and the container 311 are adaptable for connection to a hydrophilic filter 316. The chamber 301 is connected to the container 311 by connecting the chamber outlet 303 to the container inlet 312. The hydrophilic filter 316 is connected to the chamber 301 or the container 311 by connecting either the chamber outlet 303 or the container outlet 313 to the hydrophilic filter inlet 317.

It should be appreciated that the controlled source of pressure can be a source of positive or negative pressure. As such, a controlled source of negative pressure 322 can be attached indirectly to the chamber outlet 303. In one example, the controlled source of negative pressure is indirectly connected to the chamber outlet 303 through the container outlet 313. In another example, the controlled source of negative pressure 321 is indirectly connected to the chamber outlet 303 through hydrophilic filter vacuum port 315. In another example, the controlled source of negative pressure is indirectly connected to the chamber outlet 303 through any other indirect connection known to one of skill in the art including, but not limited to, a trap or condenser.

A description of the chamber 301 is given above. The container 311 is a cylinder that is pressurizable up to at least 200 psi. The dimensions of the container 311 are approximately the same as the dimensions of the chamber 301. The container may be comprised of glass. The function of the container 311 is to collect leachate 314 from a sample 310 that is displaced when pressurizing the sample 310 to the predetermined pressures as described above in the method 300 discussed in connection with FIG. 3.

It should be appreciated that the container 311 can be a pressurizable container of any size, configuration and material that will provide the intended function of the present invention. In one example, the entire structure of the container 311 is stainless steel. In another example, the container 301 is acrylic. In another example, the container 311 is capable of withstanding less than 200 psi. It should also be appreciated that another function of container 311 is to serve as a connection for pressurizing chamber 301 with a source of controlled negative pressure.

The hydrophilic filter 316 is a cylinder that is pressurizable to at least 200 psi. The dimensions of the hydrophilic filter 316 are approximately the same as the dimensions of the chamber 301 and the container 311. The hydrophilic filter 316 may be comprised of glass and contains a replaceable hydrophilic filter element 319 that is paper. The function of hydrophilic filter 316 is separating components from the leachate 314 that can pass through the hydrophilic filter 316 to produce soluble leachate 320.

It should be appreciated that hydrophilic filter 316 can be a pressurizable container of any size, configuration and material that will provide the intended function of the present invention. In one example, the entire structure of the hydrophilic filter 316 is stainless steel. In another example, the hydrophilic filter 316 is acrylic. In another example, the hydrophilic filter 316 is capable of withstanding less than 200 psi. In another example, the hydrophilic filter element 319 is porous glass. It should also be appreciated that another function of hydrophilic filter 316 is to serve as a connection for pressurizing chamber 301 with a source of controlled negative pressure.

The invention has been described above. The following Examples are presented to illustrate ways of determining an amount of coal tar that can enter, and subsequently be displaced from, a given type of soil for a range of depths of the soil, and verifying the pressure at which coal tar can be displaced from the given type of soil, rather than to limit the scope of the invention.

EXAMPLE 1

In order to determine the concentration of components in coal tar, extraction of MAHs and PAHs from coal tar samples from 9 MGP sites was performed using EPA method 3580 and analyzed by GC/MS with EPA method 8270, each of which are incorporated by reference herein in their entirety. Large particles of gravel, wood, and brick were removed, and the samples were homogenized by mixing in a stainless steel bowl. The concentrations of coal tar components are shown in Table 1.

TABLE 1

| | Concentrations at Particular Sites (mg/kg) | | | | | | | | |
|---|---|---|---|---|---|---|---|---|---|
| Compounds | 1 | 2 | 3 | 4 | 5 | 6 | 7 | 8 | 9 |
| Benzene | 48 | 984 | 491 | 514 | 523 | 964 | 986 | 1690 | 1360 |
| Toluene | 210 | 3690 | 2020 | 3100 | 1000 | 3330 | 2840 | 6370 | 4270 |
| Ethylbenzene | 48 | 2920 | 1330 | 901 | 251 | 647 | 1760 | 2590 | 3790 |
| m/p-Zylenes | 284 | 3120 | 1720 | 2920 | 1160 | 3020 | 2100 | 4620 | 3400 |
| Styrene | 183 | 954 | 122 | 2450 | 467 | 508 | 1110 | 3410 | 337 |
| 0-Xylene | 148 | 1610 | 728 | 1600 | 440 | 1620 | 1060 | 2180 | 1590 |
| 1,2,4Trimethylbenzene | 323 | 1950 | 884 | 1830 | 705 | 2650 | 1130 | 2710 | 2410 |
| Naphthalene | 10000 | 32700 | 7770 | 20600 | 27500 | 28800 | 13900 | 56100 | 68200 |
| 2-Methylnaphthalene | 4660 | 19000 | 5270 | 12300 | 6860 | 27000 | 8620 | 24000 | 38300 |
| 1-Methylnaphthalene | 2870 | 16200 | 3330 | 8900 | 3930 | 17400 | 5530 | 14000 | 24300 |
| Acenaphthylene | 1710 | 9520 | 567 | 4730 | 4050 | 6600 | 2430 | 8040 | 20000 |
| Acenaphthene | 430 | 1880 | 1150 | 612 | 928 | 1330 | 559 | 959 | 2300 |
| Dibenzofuran | 1520 | 1030 | 185 | 1000 | 5250 | 1040 | 180 | 421 | 2505 |
| Fluorene | 2420 | 6320 | 716 | 2730 | 2960 | 4540 | 1370 | 2540 | 9510 |
| Phenanthrene | 5570 | 17300 | 2160 | 8010 | 10400 | 14200 | 4080 | 9830 | 27200 |
| Anthracene | 1670 | 5170 | 634 | 2780 | 3090 | 4020 | 1210 | 2970 | 8310 |
| Fluoranthene | 2870 | 5240 | 572 | 2550 | 6220 | 2390 | 1330 | 3070 | 8690 |
| Pyrene | 2100 | 7150 | 762 | 3200 | 5110 | 4260 | 2200 | 4750 | 11400 |
| Benz[a]anthracene | 1110 | 3600 | 347 | 1680 | 2440 | 1210 | 1020 | 1950 | 4390 |
| Chrysene | 802 | 3930 | 339 | 1430 | 2250 | 1080 | 979 | 1840 | 3850 |
| Benzo[b]fluoranthene | 481 | 1170 | 136 | 638 | 1630 | 329 | 389 | 735 | 1930 |
| Benzo[k]fluoranthene | 695 | 1650 | 156 | 712 | 1780 | 413 | 419 | 1060 | 2420 |
| Benzo[a]pyrene | 678 | 2610 | 268 | 1150 | 2340 | 816 | 864 | 1960 | 4100 |
| Indeno[1,2,3cd]pyrene | 311 | 797 | 85 | 371 | 1270 | 202 | 295 | 671 | 1530 |
| Dibenz[a,h]anthracene | 94 | 346 | 34 | 151 | 366 | 80 | 124 | 222 | 463 |
| Benzo[g,h,i]perylene | 351 | 1000 | 100 | 465 | 1400 | 251 | 487 | 898 | 1930 |

The contaminants of most interest in Table 1 are (1) MAHs including, but not limited to, benzene, toluene, ethylbenzene, and o-xylene; (2) PAHs with two or three rings including, but not limited to, naphthalene, fluorene, anthracene, and phenthrene; and (3) PAHs with four rings or higher including, but not limited to, fluoranthene and pyrene.

EXAMPLE 2

Figure 6:
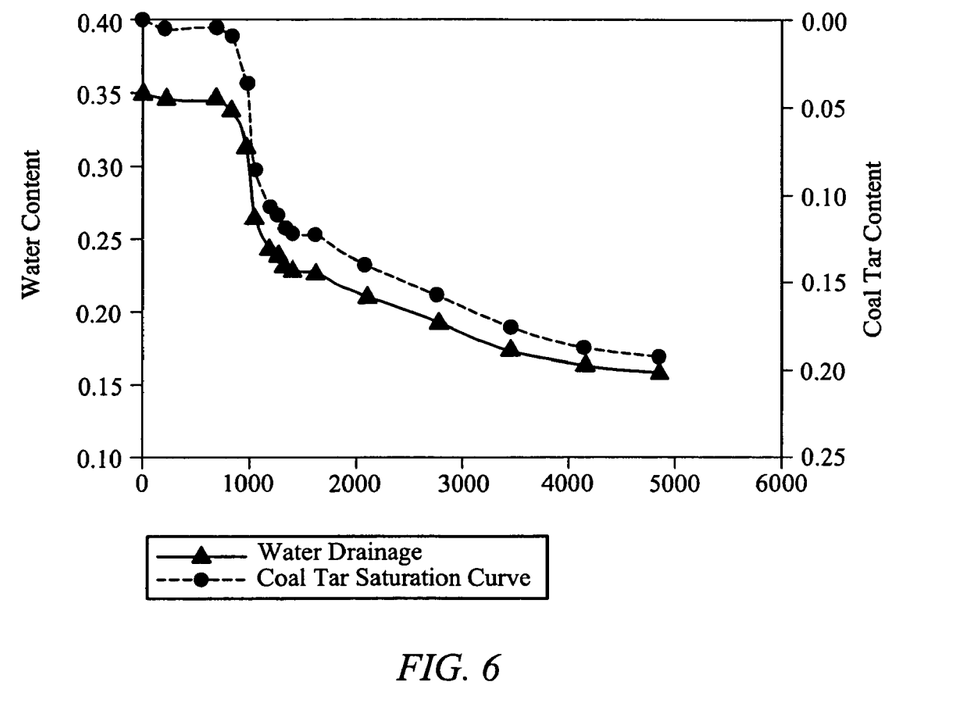
FIG. 6 is an example of a coal tar injection curve.

FIG. 6 is an example of a coal tar injection curve. It illustrates the drainage of water and the imbibition of coal tar. In this case the residual saturation of coal tar is approximately at 18% and 5000 mm Hg.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are, therefore, to be considered in all respects as illustrative and not restrictive, the scope of the invention being indicated by the appended claims, and not limited to the foregoing description.

For example, the invention has been described above using a positive pressure such as compressed air to pressurize the chamber and feed water and coal tar into soil samples, whereas other forms of pressure may be used. In one example, a mechanical positive pressure, such as a press, may be used. In another example, a vacuum may be used. Moreover, although the invention has been described as using a particular number or shape of system components, it is to be understood that other components may be used with the system and method of the present invention. For example, the chamber may be cylindrical, square, rectangular, or any shape that allows for pressurizing a sample to displace leachate from soil. Further, it should be appreciated that multiple chambers may be used simultaneously along with multiple reservoirs, multiple containers and multiple filters.

What is claimed is:

1. A method for determining an amount of coal tar that can enter a given type of soil at a range of soil depths at a field site, comprising:
   placing a soil sample free of coal tar from a site in a pressurizable chamber;
   filling the pressurizable chamber with water, thereby displacing gas from the pressurizable chamber;

feeding coal tar at a first predetermined pressure to the pressurizable chamber, thereby pressurizing the soil sample to the first predetermined pressure and displacing a portion of the water with the coal tar to create an amount of displaced water;

measuring the amount of the displaced water to determine an amount of coal tar that entered the soil sample;

repeating the feeding coal tar and the measuring the amount of the displaced water at a plurality of additional predetermined pressures to provide a plurality of pressures and corresponding amounts of coal tar that entered the soil sample; and correlating each of the pressures to a depth of soil at a field site to determine an amount of coal tar that can enter the soil at a range of soil depths at the field site.

2. The method of claim 1, further comprising determining an amount of coal tar that can be displaced from the soil sample at a range of soil depths at the field site, wherein said determining comprises:

feeding water at a first predetermined water pressure to the pressurizable chamber, thereby pressurizing the soil sample to the first predetermined water pressure and displacing a portion of the coal tar from the sample to produce an amount of displaced coal tar;

measuring the amount of displaced coal tar;

repeating the feeding water and the measuring the amount of displaced coal tar at a plurality of additional predetermined water pressures, thereby generating a plurality of water pressures and corresponding amounts of displaced coal tar; and correlating each of the water pressures to a depth of soil at the field site to determine an amount of coal tar that can be displaced from the soil sample at a range of soil depths at the field site.

3. The method of claim 2, wherein repeating the feeding water and the measuring the amount of displaced coal tar at the plurality of additional predetermined water pressures comprises determining an asymptotic minimum amount of displaced coal tar.

4. The method of claim 3, wherein the asymptotic minimum amount of displaced coal tar is associated with an asymptotic maximum amount of coal tar displaceable from the soil sample.

5. The method of claim 2, wherein the plurality of water pressures comprise a range of about 0.01 psi to about 100 psi.

6. The method of claim 2, further comprising generating a graphical representation comprising:

a first curve illustrating amounts of coal tar enterable into the soil in a range of pressures; and a second curve illustrating amounts of coal tar displaceable from the soil in the range of pressures.

7. The method of claim 6, further comprising using the graphical representation to determine a maximum amount of coal tar enterable into the soil at a predetermined depth of the soil.

8. The method of claim 6, further comprising using the graphical representation to determine a maximum amount of coal tar displaceable from the soil at a predetermined depth of the soil.

9. The method of claim 6, further comprising using the graphical representation to determine whether coal tar can be displaced from the soil given a predetermined depth and a predetermined coal tar concentration.

10. The method of claim 6, further comprising using the graphical representation to determine a concentration of coal tar in the soil given a predetermined water pressure required to displace the coal tar from the soil.

11. The method of claim 1, wherein repeating the feeding coal tar and the measuring the amount of the displaced water at the plurality of additional predetermined pressures comprises determining an asymptotic minimum amount of displaced water.

12. The method of claim 11, wherein the asymptotic minimum amount of displaced water is associated with an asymptotic maximum amount of coal tar enterable into the soil sample.

13. The method of claim 1, wherein the plurality of pressures comprise a range of about 0.01 psi to about 100 psi.

14. The method of claim 1, wherein the soil sample is obtained from a field site at a depth of up to about 300 feet.

15. The method of claim 1, further comprising generating a graphical representation illustrating an amount of coal tar enterable into the soil sample in a range of pressures.

16. A method for determining an amount of coal tar that can be displaced from a soil sample at a range of soil depths at a field site, comprising:

placing a soil sample comprising a known amount of coal tar in a pressurizable chamber;

removing gas from the soil sample;

feeding water at a first predetermined water pressure to the pressurizable chamber, thereby pressurizing the soil sample to the first predetermined water pressure and displacing a portion of the coal tar from the sample to produce an amount of displaced coal tar;

measuring the amount of displaced coal tar;

repeating the feeding water and the measuring the amount of displaced coal tar at a plurality of additional predetermined water pressures, thereby generating a plurality of water pressures and corresponding amounts of displaced coal tar; and correlating each of the water pressures to a depth of soil at the field site to determine an amount of coal tar that can be displaced from the soil sample at a range of soil depths at the field site.

\* \* \* \* \*